(12) United States Patent
Chase et al.

(10) Patent No.: US 10,994,263 B2
(45) Date of Patent: May 4, 2021

(54) POLARIZED FIBER MATS FOR CATALYST SUPPORT STRUCTURES

(71) Applicants: George Chase, Wadsworth, OH (US); Dinesh Lolla, Oxnard (CA); Ahmed Abutaleb, Jazan (SA)

(72) Inventors: George Chase, Wadsworth, OH (US); Dinesh Lolla, Oxnard (CA); Ahmed Abutaleb, Jazan (SA)

(73) Assignee: The University of Akron, Akron, OH (US)

( * ) Notice: Subject to any disclaimer, the term of this patent is extended or adjusted under 35 U.S.C. 154(b) by 210 days.

(21) Appl. No.: 16/130,008

(22) Filed: Sep. 13, 2018

(65) Prior Publication Data

US 2019/0076825 A1 Mar. 14, 2019

Related U.S. Application Data

(60) Provisional application No. 62/558,058, filed on Sep. 13, 2017.

(51) Int. Cl.
*C07C 49/403* (2006.01)
*B01J 23/44* (2006.01)
(Continued)

(52) U.S. Cl.
CPC ............. *B01J 23/44* (2013.01); *B01J 21/063* (2013.01); *B01J 23/42* (2013.01); *B01J 23/462* (2013.01);
(Continued)

(58) Field of Classification Search
CPC ...... B01J 37/342; B01J 37/347; B01J 31/063; B01J 23/44; B01J 31/06; B01J 35/0013; B01J 35/0033; B01J 35/06; B01J 37/08; B01J 37/0209; B01J 37/0207; B01J 20/321; B01J 20/3208; B01J 20/3293;
(Continued)

(56) References Cited

U.S. PATENT DOCUMENTS

| 2011/0052467 A1* | 3/2011 | Chase .................... B01J 35/06 423/239.1 |
| 2014/0128251 A1* | 5/2014 | Sawa ..................... B01J 35/006 502/159 |
| 2017/0250431 A1* | 8/2017 | Pintauro ............. H01M 4/8652 |

FOREIGN PATENT DOCUMENTS

| CN | 1584135 A | * | 2/2005 |
| CN | 101279204 A | * | 10/2008 |

OTHER PUBLICATIONS

Machine Translation of CN-1584135-A (Year: 2020).*
(Continued)

*Primary Examiner* — David M Brunsman
(74) *Attorney, Agent, or Firm* — Renner Kenner Greive Bobak Taylor & Weber

(57) ABSTRACT

A polymer-catalyst assembly includes polarized polymeric nanofibers retaining a plurality of catalytic metallic nanoparticles. A method of making the polarized polymer-catalyst assembly may include providing a fiber mat having polymeric nanofibers retaining a plurality of catalytic metallic nanoparticles, stretching the fiber mat in a uniaxial direction, simultaneous with the step of stretching, thermally heating the fiber mat, simultaneous with the steps of stretching and thermally heating, subjecting the fiber mat to an electric field, whereby the simultaneous steps of stretching, thermally heating, and subjecting thereby form a polarized fiber mat.

20 Claims, 5 Drawing Sheets

(51) Int. Cl.
  *B01J 35/06*   (2006.01)
  *B01J 35/00*   (2006.01)
  *B01J 37/34*   (2006.01)
  *B01J 37/02*   (2006.01)
  *B01J 31/06*   (2006.01)
  *B01J 37/08*   (2006.01)
  *B01J 23/46*   (2006.01)
  *B01J 21/06*   (2006.01)
  *B01J 23/42*   (2006.01)
  *B01J 23/52*   (2006.01)

(52) U.S. Cl.
  CPC ........... *B01J 23/464* (2013.01); *B01J 23/466* (2013.01); *B01J 23/468* (2013.01); *B01J 23/52* (2013.01); *B01J 31/06* (2013.01); *B01J 35/0013* (2013.01); *B01J 35/0033* (2013.01); *B01J 35/06* (2013.01); *B01J 37/0207* (2013.01); *B01J 37/0209* (2013.01); *B01J 37/08* (2013.01); *B01J 37/342* (2013.01); *B01J 37/347* (2013.01); *C07C 49/403* (2013.01); *B01J 31/063* (2013.01)

(58) Field of Classification Search
  CPC ........ B01J 21/063; B01J 23/42; B01J 23/462; B01J 23/464; B01J 23/466; B01J 23/468; B01J 23/75; B01J 23/755; C07C 49/403
  See application file for complete search history.

(56) References Cited

OTHER PUBLICATIONS

Machine Translation CN-101279204-A (Year: 2020).*
Ili et al, "Electrospinning of Nanofibers:Reinventing the Wheel?", Adv. Mater. 2004, 16, No. 14, Jul. 19, 2004.*

* cited by examiner

POLARIZED FIBER MATS FOR CATALYST SUPPORT STRUCTURES

CROSS-REFERENCE TO RELATED APPLICATIONS

The present application claims the benefit of U.S. Provisional Patent Application No. 62/558,058, filed Sep. 13, 2017, incorporated herein by reference.

FIELD OF THE INVENTION

Embodiments of the invention are directed toward polymer-catalyst assemblies including polarized fibers retaining a catalyst. The polymer-catalyst assemblies may be particularly useful for polar molecule capture from aqueous based solutions, such as for hydrogenation conversion reactions.

BACKGROUND OF THE INVENTION

Metal and metal oxide nanoparticles have excellent catalytic properties. However, when utilized independently as catalysts, these nanoparticles generally do not possess good mechanical strength and chemical stability. This independent use also suffers from extremely high pressure drop, particularly when utilized within fixed-bed columns, and aggregation of the nanoparticles, which decreases their high surface area to volume ratio and reduces their effectiveness.

To overcome these detriments, the metal and metal oxide nanoparticles have been distributed into natural and synthetic polymers. This has overcome many of the identified problems without affecting their characteristics. Examples include palladium nanoparticles on polyaniline polymer support for particular use with the Suzuki reaction and platinum nanoparticles on polyetherimide polymer support for particular use with the hydrogenation of soybean oil.

Other known examples of utilizing catalyst particles include platinum nanoparticles supported on mesoporous silica (MS), titanate nanotubes (TNT); palladium particles on carbon nanotubes; and palladium and platinum nanoparticles supported on poly(2,6-dimethyl-1,4-phenylene) oxide electrospun membranes. However, these examples suffer from one or more disadvantages, such as requiring modifying the surface of the support with oxygen-containing groups to change the catalytic support properties.

Thus, there remains a need in the art for an improved mechanism for utilizing catalyst particles.

SUMMARY OF THE INVENTION

In a first embodiment, the present invention provides a polymer-catalyst assembly comprising polarized polymeric nanofibers retaining a plurality of catalytic metallic nanoparticles.

In a second embodiment, the present invention provides a polymer-catalyst assembly as in any of the above embodiments, wherein the polarized polymeric nanofibers are made of a polymer selected from the group consisting of polyvinylidene fluoride (PVDF), poly(vinylidene fluoride-co-hexafluoropropylene) (PVDF-HFP), polymethyl methacrylate (PMMA), polyvinylchloride (PVC), polytetraflouroethylene (PTFE), polyethylene terephthalate (PET), polystyrene, polyethylene, polypropylene (PP), polycarbonate (PC), polysulfone (PS), and polyamides.

In a third embodiment, the present invention provides a polymer-catalyst assembly as in any of the above embodiments, wherein the polarized polymeric nanofibers are made of polyvinylidene fluoride.

In a fourth embodiment, the present invention provides a polymer-catalyst assembly as in any of the above embodiments, wherein the catalytic metallic nanoparticles are made of a metal selected from the group consisting of Ni, Rh, Ru, Co, Ir, Pt, Os, Pd, Au, Pt, Ti, and Ir.

In a fifth embodiment, the present invention provides a polymer-catalyst assembly as in any of the above embodiments, wherein the catalytic metallic nanoparticles are made of a metal oxide selected from the group consisting of oxides of Ni, Rh, Ru, Co, Ir, Pt, Os, Pd, Au, Pt, Ti, and Ir.

In a sixth embodiment, the present invention provides a polymer-catalyst assembly as in any of the above embodiments, wherein the catalytic metallic nanoparticles are made of Pd.

In a seventh embodiment, the present invention provides a polymer-catalyst assembly as in any of the above embodiments, wherein the polarization of polymer-catalyst assembly is characterized by an electric dipole moment of from $4.63 \times 10^{-12}$ coulomb-meter (C·m) to $7.35 \times 10^{-12}$ C·m.

In an eighth embodiment, the present invention provides a polymer-catalyst assembly as in any of the above embodiments, wherein the polarized polymeric nanofibers have a mean average cross-sectional diameter of from 50 nm to 300 nm.

In a ninth embodiment, the present invention provides a method of making the polymer-catalyst assembly as in any of the above embodiments, comprising providing a fiber mat having polymeric nanofibers retaining a plurality of catalytic metallic nanoparticles, stretching the fiber mat in a uniaxial direction, simultaneous with the step of stretching, thermally heating the fiber mat, simultaneous with the steps of stretching and thermally heating, subjecting the fiber mat to an electric field, whereby the simultaneous steps of stretching, thermally heating, and subjecting thereby form a polarized fiber mat.

In a tenth embodiment, the present invention provides a method as in any of the above embodiments, wherein the step of providing the fiber mat includes electrospinning a spinnable solution to form an electrospun fiber mat.

In an eleventh embodiment, the present invention provides a method as in any of the above embodiments, wherein the step of providing the fiber mat includes soaking the electrospun fiber mat in a solution containing a precursor of the catalytic metallic nanoparticles, the method further comprising a step of reducing the precursor to form the catalytic metallic nanoparticles.

In a twelfth embodiment, the present invention provides a method as in any of the above embodiments, the fiber mat having an un-stretched length, wherein the step of stretching the fiber mat includes stretching the fiber mat from 1.1 to 1.15 times the un-stretched length.

In a thirteenth embodiment, the present invention provides a method as in any of the above embodiments, wherein the step of thermally heating the fiber mat includes subjecting the fiber mat to a constant temperature ramp rate of from 15° C./min to 25° C./min.

In a fourteenth embodiment, the present invention provides a method as in any of the above embodiments, wherein the electric field is in a range of from 2 kV/cm to 3 kV/cm.

In a fifteenth embodiment, the present invention provides a method as in any of the above embodiments, further comprising a step of cooling the polarized fiber mat.

In a sixteenth embodiment, the present invention provides a method as in any of the above embodiments, further comprising a step of providing a reaction fluid containing phenol to the polarized fiber mat.

In a seventeenth embodiment, the present invention provides a method as in any of the above embodiments, wherein the step of providing a reaction fluid containing phenol to the polarized fiber mat achieves substantially complete conversion of phenol.

In an eighteenth embodiment, the present invention provides a method as in any of the above embodiments, wherein the step of providing a reaction fluid containing phenol to the polarized fiber mat achieves substantially complete conversion of phenol to cyclohexanone within 9 hours reaction time.

In a nineteenth embodiment, the present invention provides a method as in any of the above embodiments, wherein the step of providing a reaction fluid containing phenol to the polarized fiber mat achieves substantially complete selectivity of cyclohexanone.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

Embodiments of the invention are based on polymer-catalyst assemblies and corresponding methods of manufacture and methods of operation. The polymer-catalyst assemblies may be particularly useful for capturing polar molecules from aqueous based solutions having the polar molecules, such as for hydrogenation conversion reactions.

Figure 1:
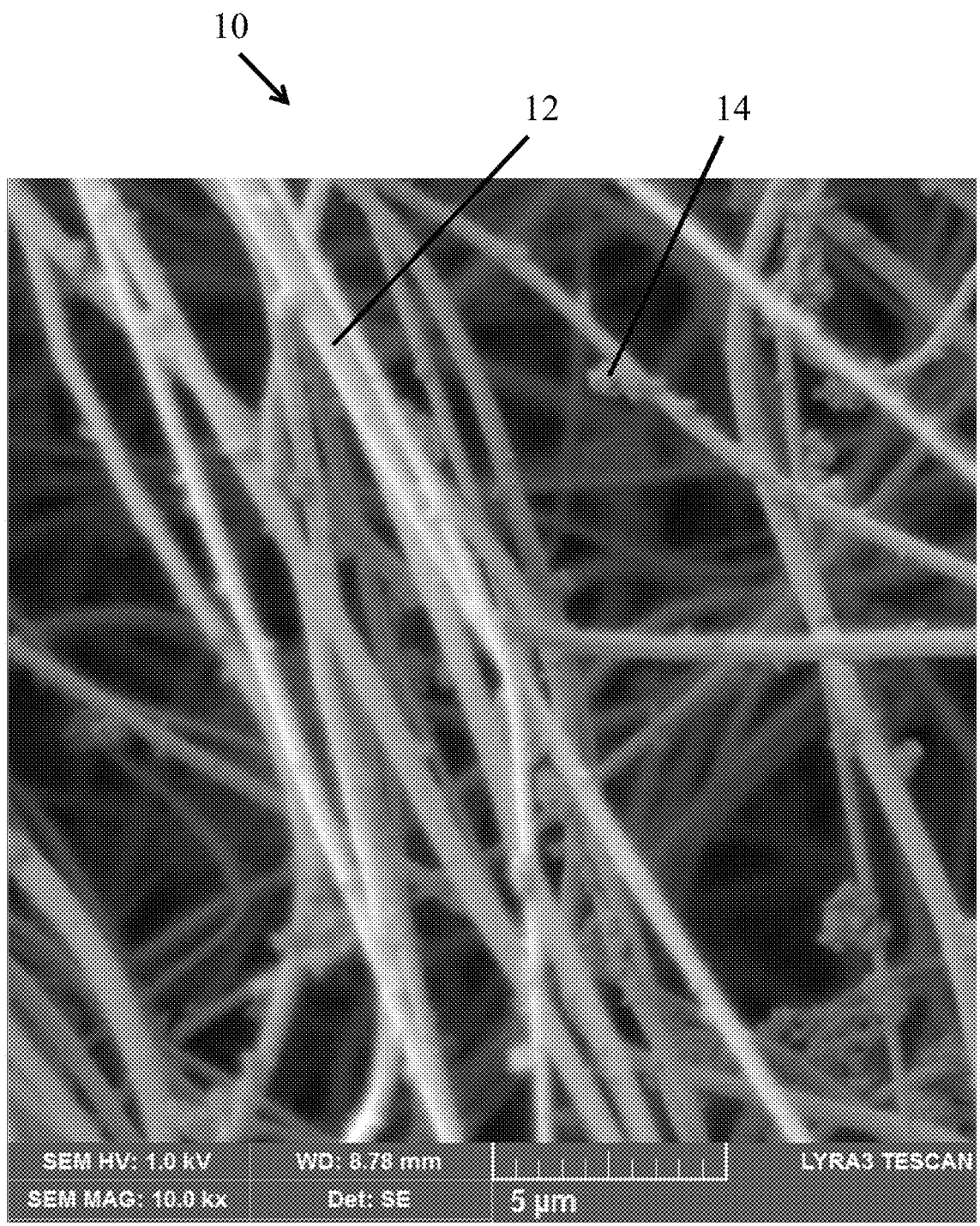
FIG. 1 is an SEM micrograph of a polymer-catalyst assembly of embodiments of the present invention.
Figure 2:
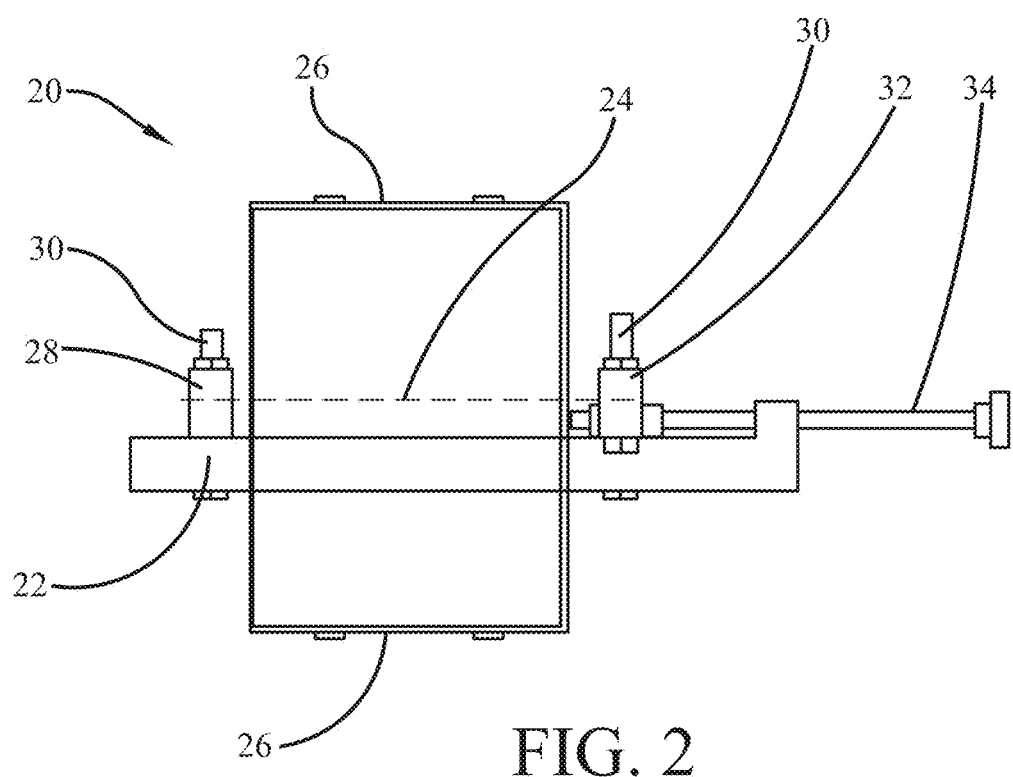
FIG. 2 is a side view of a polarizing assembly of embodiments of the present invention.
Figure 3:
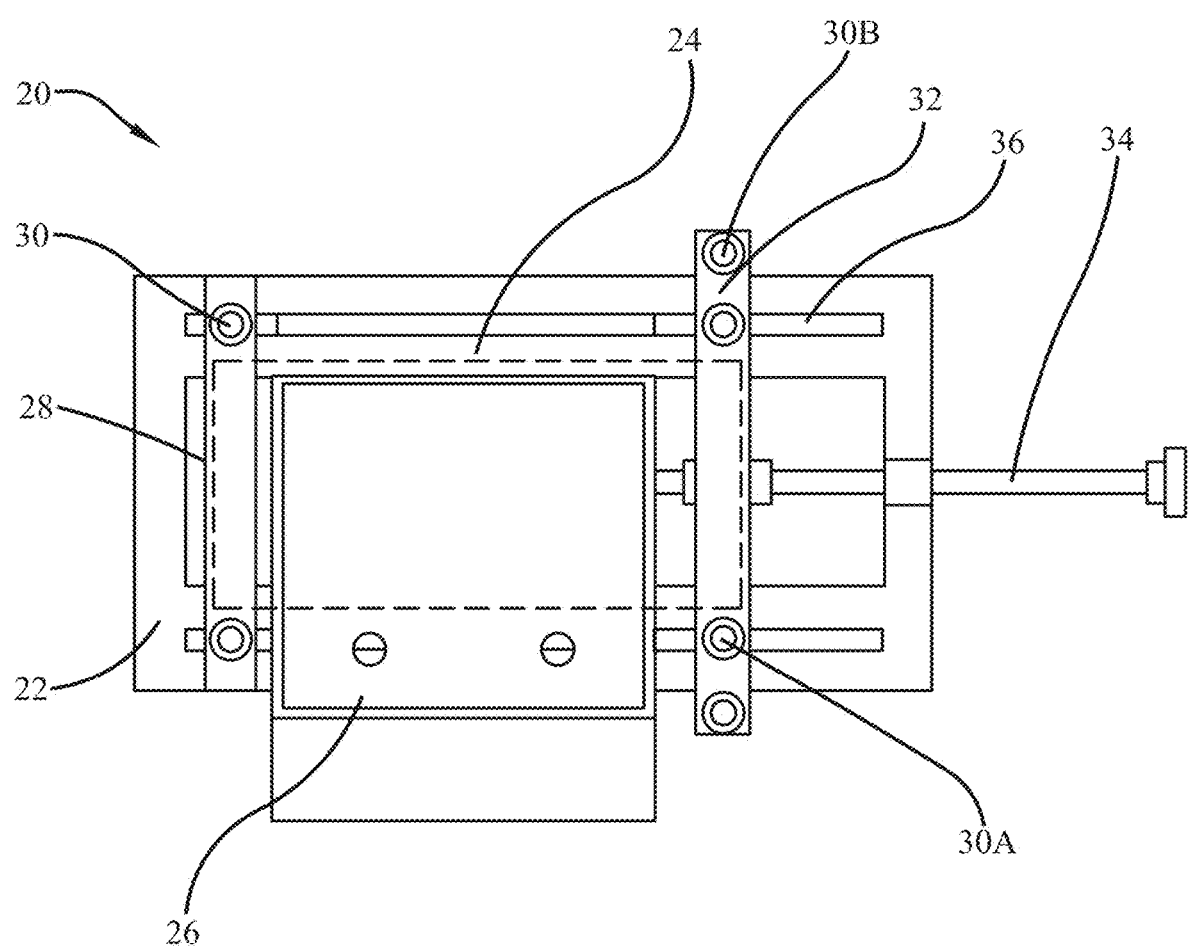
FIG. 3 is a top view of the polarizing assembly of FIG. 2.
Figure 4:
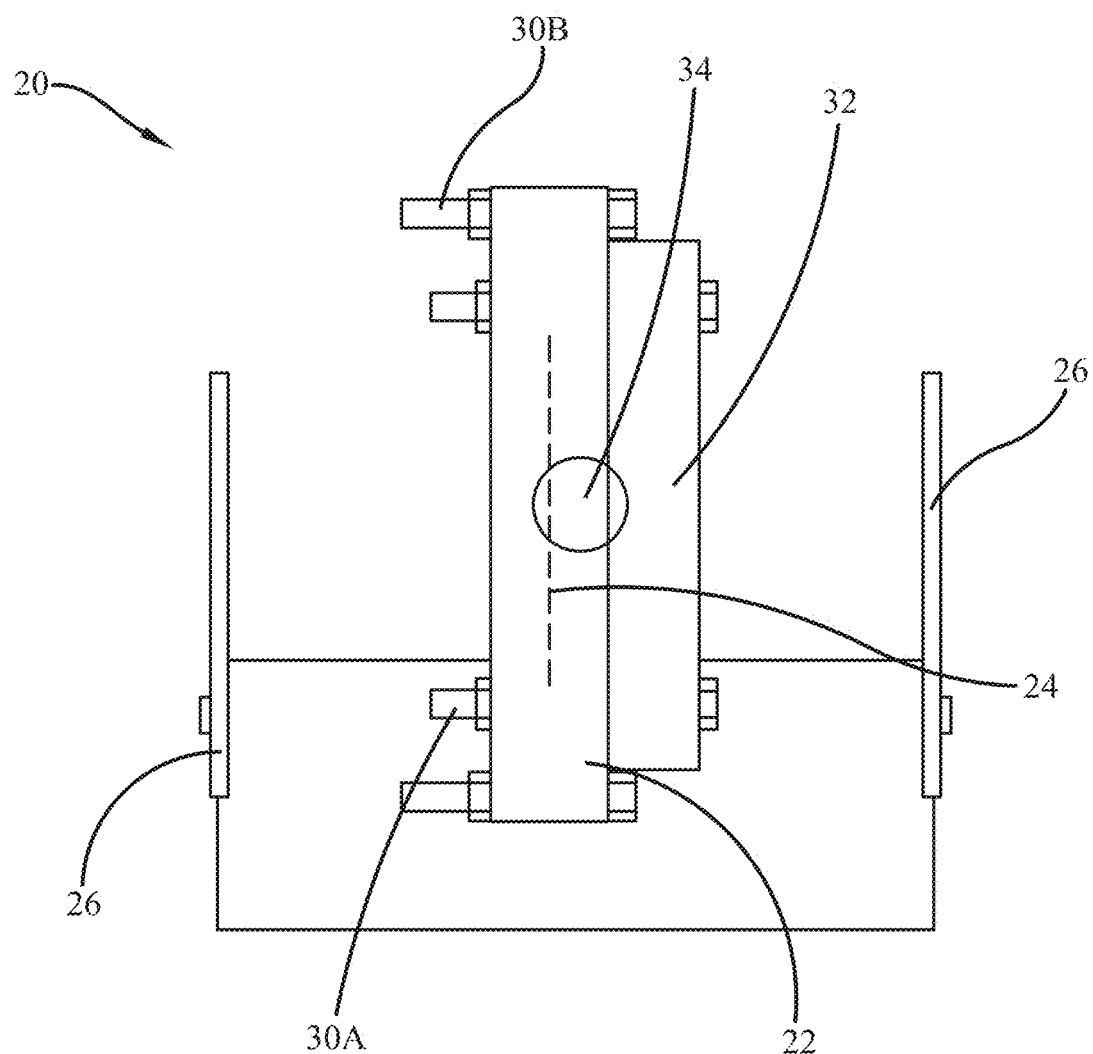
FIG. 4 is a front view of the polarizing assembly of FIG. 2.

With reference to FIG. 1, a polymer-catalyst assembly 10 includes polarized fibers 12 retaining a catalyst 14. In one or more embodiments, polymer-catalyst assembly 10, which may also be referred to as a polymer supported nanoparticle (PSNP) system 10, may be in the form of a fiber mat made of polarized fibers 12. Polarized fibers 12 may be subjected to induced dipole moment by a process including simultaneous heating (and subsequent cooling), stretching, and subjection to a strong electric field, as will be further described herein.

The retained catalyst 14, which may be described as metal nanoparticles 14 or metal oxide nanoparticles 14, maintains the intrinsic properties even down to the nanoscale level. Based on the polarization of polarized fibers 12, when an aqueous based solution having polar organic molecules therein is provided to polymer-catalyst assembly 10, the polar organic materials are attracted to polarized fibers 12. Following this attraction, catalyst 14 can thereby function to catalyze a reaction of the polar organic molecules to a reaction product. This attraction can serve to enhance the reaction rates of catalyst 14 by increasing reactant concentrations near catalyst 14. Furthermore, when a product of the reaction is non-polar or less polar than the reactants, this non-polar or less polar product will be displaced away from polarized fibers 12, thereby further enhancing the catalyst performance in terms of reaction rate, conversion, and selectivity.

In one or more embodiments, polymer-catalyst assembly 10 can be made by a method including forming fibers, such as by electrospinning a spinnable solution, polarizing the electrospun fibers to thereby form polarized fibers 12, and impregnating polarized fibers 12 with catalyst 14.

In one or more embodiments, fibers which will eventually form polarized fibers 12 are formed by electrospinning a spinnable solution or liquid. Electrospinning may be preferred for forming fibers due to its simplicity, ease of maintenance, and low cost of production. Details related to electrospinning are generally known by the skilled person. An exemplary electrospinning process is wire-loop electrospinning. An electrospinning apparatus can generally include a high voltage DC power supply, a capillary tube with a small diameter needle, and a collector, which may be stationary or rotating. Certain electrospinning processes are syringe-less or nozzle-less. Once received by the collector, the fibers may be described as an electrospun non-woven or an electrospun fiber mat. One or more aspects of an electrospinning process may be disclosed by U.S. Pat. Nos. 7,585,437; 8,157,554; 8,231,822; and 8,573,959, which are incorporated herein by reference.

Exemplary polymers that may be included in the spinnable solution to thereby form the fibers include polyvinylidene fluoride (PVDF), poly(vinylidene fluoride-co-hexafluoropropylene) (PVDF-HFP), polymethyl methacrylate (PMMA), polyvinylchloride (PVC), polytetraflouroethylene (PTFE), polyethylene terephthalate (PET), polystyrene, polyethylene, polypropylene (PP), polycarbonate (PC), polysulfone (PS), polyamides, such as aliphatic or semi-aromatic polyamides known under the generic designation of nylon, polyimides, polymethylsiloxane, epoxide resin, and combinations thereof.

In one or more embodiments, the spinnable solution is formed from one or more polymers dissolved in one or more solvents. The particular one or more polymers and one or more solvents can be chosen based on the corresponding properties. In one or more embodiments, two or more solvents are used in the spinnable liquid to produce synergistic effects.

Suitable solvents will be appreciated as being useful for particular polymers. In accordance with the list of polymers provided herein, suitable solvents can be chosen from toluene, tetrahydrofuran (THF), dichloromethane (DCM), chloroform ($CHCl_3$), alcohols including methanol, ethanol, and propanol, dimethylacetamide (DMAC), dimethyl sulfoxide (DMSO), dimethylformamide (DMF), 2-butanone, 1-butyl-3-methylimidazolium chloride, xylene, acetone, formic acid, distilled water, trifluoracetic acid, hexafluoro-2-propanol, ionic liquids, and mixtures thereof. In one or more embodiments, a mixture of two solvents may be provided at a ratio of about 50:50.

In one or more embodiments, the polymer or polymers are present in the spinnable solution at a concentration suitable for providing acceptable solution properties, such as viscosity, conductivity, and surface tension, suitable for successful electrospinning. The molecular weight and molecular weight distribution and architecture of the polymer or polymers can also be varied to achieve a desired electrospinning.

In one or more embodiments, the polymer or polymers are present in the spinnable solution at a percentage of from 10 wt. % or more to 11 wt. % or less, in other embodiments, from 5 wt. % or more to 10 wt. % or less, and in other embodiments, from 5 wt. % or more to 15 wt. % or less.

Electrospinning produces continuous long single fibers with relatively small diameters ranging from a few nanometers to about 10 microns. As generally known in the art, parameters of an electrospinning process can be varied to alter the properties of the fibers and fiber mats. Exemplary parameters that may be adjusted include fiber diameter, internal porosity, surface charges, and formation of beads.

In one or more embodiments, an electrospinning process utilizes an applied voltage in a range of from 10 kV to 25 kV, in other embodiments, from 15 kV to 20 kV, and in other embodiments, 17 kV or approximate thereto. In one or more embodiments, an electrospinning process utilizes a tip to collector distance in a range of from 10 cm to 30 cm, in other embodiments, from 15 cm to 25 cm, and in other embodiments, 20 cm or approximate thereto. In one or more embodiments, an electrospinning process utilizes a drum rotation speed in a range of from 75 RPM to 125 RPM, in other embodiments, from 90 RPM to 110 RPM, and in other embodiments, 100 RPM or approximate thereto. In one or more embodiments, an electrospinning process utilizes a syringe flow rate in a range of from 3 mL/hr to 10 mL/hr, in other embodiments, from 4 mL/hr to 6 mL/hr, and in other embodiments, 5 mL/hr or approximate thereto. In one or more embodiments, an electrospinning process has humidity in a range of from 35% to 50%, in other embodiments, from 40% to 45%, and in other embodiments, 43% or approximate thereto. In one or more embodiments, an electrospinning process has temperature in a range of from 15° C. to 30° C., in other embodiments, from 20° C. to 25° C., and in other embodiments, 22° C. or approximate thereto.

In certain embodiments, the catalyst may be provided to a polymer solution before the fibers are made. In other embodiments, the catalyst may be provided to the fibers after the fibers are made. The methods to provide the catalyst to the polymer solution or fibers may be either an ex-situ process or an in-situ process.

Ex-situ methods use a physical treatment to imbed the catalytic nanoparticles on to the polymer substrate. Exemplary physical processes include processing steps such as casting and solvent evaporation, chemical polymerization, or co-precipitation. These physical processes may help in stabilizing the catalytic nanoparticles by preventing them from agglomeration in to larger particles.

There are three main steps involved in incorporating catalytic nanoparticles on a polymer substrate using an ex-situ method. First, the catalytic nanoparticles, which may be a precursor of an active catalyst, are mixed with a polymer solution. Then, the polymer-nanoparticles composite is produced. Then, the catalytic nanoparticles may be reduced to convert the metal salts of the catalytic material into pure active metals. Suitable techniques to reduce the catalytic nanoparticles are generally known to the skilled person.

In-situ processes may be advantageous in certain embodiments based on having fewer limitations than an ex-situ process. There are three main steps involved in incorporating catalytic nanoparticles on a polymer substrate using an in-situ method. First, the polymer substrate is made. Then, the metal or metal oxide nanoparticles, which may be a precursor of an active catalyst, may be imbedded with the polymer substrate. Then, the catalytic nanoparticles may be reduced to convert the metal salts of the catalytic material into pure active metals.

In certain embodiments, the nanoparticles can be imbedded with the fibers of the polymer substrate by soaking the polymer substrate in a metal nanoparticles precursor solution. In the soaking process, there is no chemical interaction between the metal ions/precursor and functional groups that may be present on the polymer of the polymer substrate. The nanoparticles are instead trapped and imbedded by chemical precipitation. The nanoparticles may also be entrapped in open pores between layers of the fibers of the polymer substrate.

A wet impregnation technique may include dissolving catalytic nanoparticles in a solvent to obtain uniform dispersion of particles. Then, the polymer substrate is immersed in the solvent having particles therein to impregnate particles with the fibers. Suitable amounts of the catalytic nanoparticles, solvent, and polymer will be generally known to the skilled person.

Following formation of the fibers, and providing the catalyst to the fibers, the fibers retaining the catalyst are subjected to a method of polarizing the fibers. As generally known to the skilled person, polarization may be interpreted as inducing a dipole moment in the fibers. A polarization method can include subjecting the fibers to simultaneous thermal heating (and subsequent cooling) and uniaxial stretching while present in a strong static electric field.

With reference to the Figures, a polarization apparatus 20 may be utilized for the polarization method, though other suitable apparatuses for polarization may be known to the skilled person. A frame 22 holds a fiber-catalyst sample 24, such as a fiber mat 24, between a pair of electrodes 26, with one electrode 26 as a positive electrode and one electrode 26 as a negative electrode. Frame 22 and electrodes 26 may be made from any suitable material, such as polytetrafluoroethylene (PTFE—sold under trade name Teflon®) for frame 22 and aluminum for electrodes 26. PTFE for frame 22 may offer ease of machining and low electrical conductivity at the desired temperature operation range.

Upon completion of the polarization process described herein, fiber-catalyst sample 24 becomes the polarized polymer-catalyst assembly 10 described elsewhere herein. Fiber-catalyst sample 24 may be made from any of the suitable polymers described herein. Fiber-catalyst sample 24 can be in the shape of a rectangle having a first end and a second end. The first end of fiber-catalyst 24 can be secured by a fixed clamp 28 with one or more securing mechanisms 30, such as a screw and nut. A second end of fiber-catalyst sample 24 can be secured by a movable clamp 32 with one or more securing mechanisms 30, such as a screw and nut.

Fiber mat 24 can then be stretched by moving movable clamp 32 with respect to fixed clamp 28. A long screw 34 is threaded through movable clamp 32 such that rotation of long screw 34 causes movement of movable clamp 32 about a pair of guide channels 36 within frame 22. A pair of inner securing mechanisms 30A may be partially provided within a respective guide channel 36 to direct travel of movable clamp 32. As long screw 34 rotates to move movable clamp 32, inner securing mechanisms 30A move within the respective guide channel 36 away from fixed clamp 28. Fiber mat 24 is thereby stretched in the same direction as movable clamp 32 travels, which may be described as a uniaxial direction. To maintain fiber mat 24 in the stretched position, inner securing mechanisms 30A and/or outer securing mechanisms 30B may be tightened to bear against frame 22.

In one or more embodiments, a polarization method may be characterized by the percent stretching of fiber mat 24 from the un-stretched position to the stretched position. In one or more embodiments, fiber mat 24 may be stretched about 1.1 times its un-stretched length, and in other embodiments, about 1.15 times its un-stretched length. In one or more embodiments, fiber mat 24 may be stretched at least 1.1 times its un-stretched length and in other embodiments, at least 1.15 times its un-stretched length. In one or more embodiments, fiber mat 24 may be stretched in a range of from 1.05 times to 1.2 times its un-stretched length, and in other embodiments, from 1.1 times to 1.15 times its un-stretched length.

To accomplish simultaneous thermal heating and uniaxial stretching for the polarization process, polarization apparatus 20 may be positioned in a furnace. Other heating methods are also generally known to the skilled person. While fiber mat 24 is being stretched, fiber mat 24, and in some embodiments the entire polarization apparatus 20, may be heated at a constant ramp rate. In one or more embodiments, the constant temperature ramp rate may be at least 20° C./min, and in other embodiments, 20° C./min or approximate thereto. In one or more embodiments, the constant temperature ramp rate may be in a range of from 15° C./min to 25° C./min, and in other embodiments, in a range of from 15° C./min to 20° C./min, in other embodiments, in a range of from 20° C./min to 25° C./min.

Fiber mat 24, and in some embodiments the entire polarization apparatus 20, may be heated until fiber mat 24 reaches its Curie temperature, which is known in the art as the temperature above which certain materials lose their permanent magnetic properties, to be replaced by induced magnetism. In one or more embodiments, fiber mat is heated to at least 150° C., and in other embodiments, to at least 155° C. In one or more embodiments, fiber mat is heated to about 150° C., and in other embodiments, to about 155° C. In one or more embodiments, fiber mat is heated to a range of from 145° C. to 150° C., and in other embodiments, to a range of from 150° C. to 155° C.

The Curie temperature may also be described as the temperature at which the material exhibits maximum dipole moments due to thermally driven motions of atoms, with the simultaneous stretching based on the elastic limits of the material to generate piezo-electric charge in the fibers of fiber mat 24. Elastic limits of the fibers of fiber mat 24 can be determined by stress/strain experiments. As will be further described herein, certain materials utilized for the fibers of fiber mat 24 (e.g. PVDF) exhibit piezo-electric, pyro-electric, and ferro-electric properties, which makes these materials particularly suitable for polarization by the herein described polarization method.

Fiber mat 24, and in some embodiments the entire polarization apparatus 20, may then be held at the Curie temperature for a predetermined time period. In one or more embodiments, fiber mat 24 is held at the Curie temperature for at least 20 minutes, in other embodiments, for at least 25 minutes, and in other embodiments, for at least 30 minutes. In one or more embodiments, fiber mat 24 is held at the Curie temperature for 20 minutes or approximate thereto, for 25 minutes or approximate thereto, and in other embodiments, for 30 minutes or approximate thereto. In one or more embodiments, fiber mat 24 is held at the Curie temperature for a range of from 15 min to 20 min, in other embodiments, from 15 min to 30 min, and in other embodiments, from 20 min to 30 min.

Fiber mat 24, and in some embodiments the entire polarization apparatus 20, may be cooled at a constant cooling rate. In one or more embodiments, the constant temperature cooling rate may be at least 20° C./min, and in other embodiments, at least 30° C./min. In one or more embodiments, the constant temperature cooling rate may be 20° C./min or approximate thereto, and in other embodiments, 30° C./min or approximate thereto. In one or more embodiments, the constant temperature cooling rate may be in a range of from 15° C./min to 25° C./min, and in other embodiments, in a range of from 15° C./min to 20° C./min, in other embodiments, in a range of from 20° C./min to 25° C./min.

As mentioned above, the simultaneous thermal heating (and subsequent cooling) and uniaxial stretching may occur with fiber mat 24 present in a strong static electric field. The static electric field is provided by electrically charging electrodes 26 to an electric potential difference between electrodes 26. In one or more embodiments, the electric potential difference between electrodes 26 may be at least 30 kV DC, in other embodiments, at least 40 kV DC, and in other embodiments at least 50 kV DC. In one or more embodiments, the electric potential difference between electrodes 26 may be 30 kV DC or approximate thereto, in other embodiments 40 kV DC or approximate thereto, and in other embodiments 50 kV DC or approximate thereto. In one or more embodiments, the electric potential difference between electrodes 26 may be in a range of from 25 kV DC to 35 kV DC, and in other embodiments, from 30 kV DC to 50 kV DC.

The electric potential difference along with the distance between electrodes 26 provides an electric field. In one or more embodiments, the distance between electrodes 26 may be at least 12 cm, in other embodiments, at least 15 cm, and in other embodiments, at least 18 cm. In one or more embodiments, the distance between electrodes 26 may be 12 cm or approximate thereto, in other embodiments, 15 cm or approximate thereto, and in other embodiments, 18 cm or approximate thereto. In one or more embodiments, the distance between electrodes 26 may be in other embodiments, in a range of from 10 cm to 14 cm, and in other embodiments, from 10 cm to 18 cm.

In one or more embodiments, the electric field generated by electrodes 26 may be at least 2.5 kV/cm, in other embodiments, at least 4 kV/cm, and in other embodiments, at least 5 kV/cm. In one or more embodiments, the electric field generated by electrodes 26 may be 2.5 kV/cm or approximate thereto, in other embodiments, 4 kV/cm or approximate thereto, in other embodiments 5 kV/cm or approximate thereto. In one or more embodiments, the electric field generated by electrodes 26 may be in a range of from 2 kV/cm to 3 kV/cm, and in other embodiments, from 2 kV/cm to 5 kV/cm.

Based on the positioning of fiber mat 24 between electrodes 26, the electric field is perpendicular to the surface of fiber mat 24. In certain embodiments, the electric potential can be applied via a DC power supply that is also used for an electrospinning apparatus. This may be accomplished by passing electrical wires through flexible insulation around a furnace door.

The applied electric field serves to enhance both the catalytic activity and selectivity of polarized polymer-catalyst assembly 10 due to sturdy interaction between the fibers of fiber mat 24 and catalyst 14 due to the strong polarization charge. The stronger the applied electric field the farther the effect extends into the pore spaces and the more effective the mechanism for particle capture.

The pair of electrodes 26 act as a parallel plate capacitor, with the electric field traveling in the direction from the positively charged electrode to the negatively charged electrode. With fiber mat 24, as a ferroelectric material, in between the two electrodes, the dipoles (two equal and opposite charges separated by a small distance) inside the fibers are initially aligned in random directions. With the application of the electric field at the elevated temperature, the majority of the dipoles align in a particular direction resulting in net polarization. The surface of the ferroelectric material (i.e. fiber mat 24) nearest to the positively charged electrode 26 contains the negative charges and vice versa. Hence there is a net change in the electric field lines due to the dipoles in the ferroelectric material. The amount of change in the electric field depends on the strength and concentration of the dipoles in the ferroelectric material. The total current between electrodes 26 may give a measure of the strength of the polarization of fiber mat 24.

Fiber mat 24 is able to retain the polarization enhancement over a predetermined time. This may also be described as fiber mat 24 having negligible polarization loss after a predetermined timeframe.

In one or more embodiments, polarized polymer-catalyst assembly 10 may be characterized by its electric dipole moment. Electric dipole moment is a measure of the separation of positive and negative electrical charges within a system, that is, a measure of the system's overall polarity. In one or more embodiments, polarized polymer-catalyst assembly 10 may have an electric dipole moment of $4.6 \times 10^{-12}$ coulomb-meter (C·m) or approximate thereto, in other embodiments, $7.3 \times 10^{-12}$ C·m or approximate thereto, and in other embodiments, $9.86 \times 10^{-12}$ C·m or approximate thereto. In one or more embodiments, polarized polymer-catalyst assembly 10 may have an electric dipole moment of from $4.6 \times 10^{-12}$ C·m to $9.86 \times 10^{-12}$ C·m, in other embodiments, from $4.63 \times 10^{-12}$ C·m to $7.35 \times 10^{-12}$ C·m, and in other embodiments, from $7.3 \times 10^{-12}$ C·m to $9.86 \times 10^{-12}$ C·m.

In one or more embodiments, polarized polymer-catalyst assembly 10 may be characterized by the contact angle of a water droplet thereon. The contact angle of a water droplet characterizes the hydrophobicity of a material. In one or more embodiments, polarized polymer-catalyst assembly 10 is a superhydrophobic material, which may be characterized as having a contact angle of a water droplet of at least 155°. In other embodiments, polymer-catalyst assembly 10 may have a contact angle of a water droplet of at least 145°, and in other embodiments, of at least 151°.

In one or more embodiments, polarized fibers 12 may be characterized as geometrically aligned, molecular oriented, polarized, super-hydrophobic fibers. Polarized fibers 12 advantageously simultaneously retain catalytic nanoparticles, attract polar compounds and molecules, and repel water molecules in aqueous based solutions.

In one or more embodiments, polarized fibers 12 may have piezo-electric, pyro-electric, and ferro-electric properties. Piezo-electricity may be defined as a property of certain materials that expand or contract due to external electric field. Some other materials have a capability of generating electrical charge when external pressure is applied. Pyro-electricity is the capability of some materials with negative glass transition temperatures, which may be defined as generating temporary voltage when they are subjected to a change in temperature. This results in modification of the alignment of atoms in the crystal geometry and polarization of material is affected. Ferro-electricity is an inherent property of certain materials, which may be defined as a capability of losing their spontaneous polarization due to an applied external electric field. Certain materials (e.g. PVDF) possess low ferro-electricity thereby requiring higher electric fields to polarize the fibers made from the materials.

In one or more embodiments, polarized fibers 12 may be characterized as an electret material. In general, an electret is defined as a permanently polarized and electrically insulating material with long-lived internal and/or external quasi-permanent surface charge. Projection of the electrical fields from the fibers into the pore openings is necessary for the electrostatic attraction mechanism to be effective.

In one or more embodiments, the polarization of polarized fibers 12 may favor enhancements of β-crystallization phase inside the nanofibers. The polarization may include both molecular and surface morphological changes associated with polarization treatment.

In one or more embodiments, polarized fibers 12 and corresponding mats may have larger pores than non-polarized fibers and mats made from similar materials. The polarized fibers 12 and mats may also have higher electrostatic charges due to internal orientations of the β-phase crystalline structures. The polarized fibers 12 and mats may also have higher capture efficiencies, lower pressure drops, and higher filtration indexes than non-polarized fibers and mats made from similar materials.

Exemplary materials for polarized fibers 12 correspond with the above list of polymers for the spinnable solution to thereby form the fibers. Exemplary polymers that may make up the polarized fibers 12 include polyvinylidene fluoride (PVDF), poly(vinylidene fluoride-co-hexafluoropropylene) (PVDF-HFP), polymethyl methacrylate (PMMA), polyvinylchloride (PVC), polytetraflouroethylene (PTFE), polyethylene terephthalate (PET), polystyrene, polyethylene, polypropylene (PP), polycarbonate (PC), polysulfone (PS), polyamides, such as aliphatic or semi-aromatic polyamides known under the generic designation of nylon, polyimides, polymethylsiloxane, epoxide resin, and combinations thereof.

Polyvinylidene fluoride is known to have five distinct polymorphs: α (TGTG'), β (TTTT), γ ($T_3GT_3G'$), δ, and ε. The α, β, and γ polymorphs and their exclusive absorption peaks may be used to characterize the increase in corresponding crystalline structures of the polarized fibers 12. Due to the mechanical stretching and strong electric field applied during the polarization process, polarized PVDF fibers are believed to have higher electroactive β-phase. Polarized fibers are also believed to have an increase at absorption peaks located at 776, 840, 881, 1071 $cm^{-1}$. Strong absorption signal is evidence of polarization induced molecular orientation changes in polarized PVDF fibers. The polarization is also believed to produce a new absorption peak at 1670 $cm^{-1}$ (β-phase).

Polyvinylidene fluoride also has a permanent electric dipole, perpendicular to the chain axis, which contributes to the strong piezoelectric, pyroelectric and ferroelectric effects. Chain twisting and other segmental motions provide mechanisms that can change the direction of dipole moments of the PVDF molecules.

In one or more embodiments, the polymer from which polarized fibers 12 are made may include one or more functional groups to thereby classify the polymer as a functional polymer. The nature of the polymer functional groups may impact the capacity to bind the catalytic material. For example, polymers with amine functional groups form strong bonding with most metal nanoparticles. Other examples of functional groups include hydroxyl, carbonyl, ether, ester, halide, amine, imine, amide, nitrile, and oxirane groups.

Polarized fibers 12 may be characterized by the cross-sectional diameter thereof. In one or more embodiments, polarized fibers 12 have a mean average cross-sectional diameter of from 50 nm to 300 nm, in other embodiments, from 150 nm to 250 nm, and in other embodiments, from 175 nm to 275 nm. In one or more embodiments, polarized fibers 12 have a mean average cross-sectional diameter of 150 nm or approximate thereto, in other embodiments, 200 nm or approximate thereto, and in other embodiments, 300 nm or approximate thereto.

Polarized fibers 12 may be characterized as nanofibers as having submicron (less than 1000 nm) cross-sectional diameters. Nanofibers are solid-state linear nanomaterials that are highly flexible and may have an aspect ratio (length to diameter ratio) greater than 1000:1. Nanofibers also generally have large surface area to volume ratio or mass ratio, high porosity, small pore size, superior directional strength, highly oriented crystalline structures, superior mechanical stiffness, and tensile strength.

Polarized fibers 12 may be characterized by the surface area thereof. In one or more embodiments, polarized fibers 12 have a surface area of from 350 $m^2$/g to 1500 $m^2$/g, in other embodiments, from 800 $m^2$/g to 1200 $m^2$/g, and in other embodiments, from 900 $m^2$/g to 1100 $m^2$/g. In one or more embodiments, polarized fibers 12 have a surface area of 360 $m^2$/g or approximate thereto, in other embodiments, 420 $m^2$/g or approximate thereto, and in other embodiments, 1000 $m^2$/g or approximate thereto. The high surface area of nanofibers provides both high catalytic activity and a capacity for the attachment or release of functional groups, absorbed molecules, ions, and nanometer scale particles of many kinds.

Polarized fibers 12 may be characterized by the internal fiber porosity, that is, the pores within individual fibers. Internal fiber porosity may be defined as a measure of the void space within the fibers, and may be given as a fraction of the volume of voids over the total volume, between 0 and 1. In one or more embodiments, polarized fibers 12 have a mean average internal fiber porosity of from 0.9 to 0.92, in other embodiments, from 0.9 to 0.94, and in other embodiments, from 0.9 to 0.98.

Polarized fibers 12 may be characterized by their wettability using water contact angles in air. In one or more embodiments, polarized fibers 12 have a mean average wettability of at least 145°, in other embodiments, at least 150°, in other embodiments, at least 155°, and in other embodiments, at least 156°.

In one or more embodiments, catalyst 14 may be characterized as metallic nanoparticles. As discussed above, the metallic nanoparticles may be wet-impregnated into the surface of polarized super-hydrophobic nanofibers.

Suitable materials for the metallic nanoparticles include Ni, Rh, Ru, Co, Ir, Pt, Os, Pd, Au, Pt, Ti, Ir, and combinations thereof. Corresponding oxides of these metals, e.g. $TiO_2$, may also be utilized. In particular embodiments, the material for the metallic nanoparticles may be selected based on having only one vacant d-orbital per atom, which makes these materials particularly suitable as having good catalytic activity during hydrogenation reactions.

Catalyst particles 14 may be characterized by the cross-sectional diameter thereof. In one or more embodiments, catalyst particles 14 have a mean average cross-sectional diameter of from 5 nm to 80 nm, in other embodiments, from 10 nm to 60 nm, and in other embodiments, from 20 nm to 80 nm.

Catalyst particles 14 may be characterized by the amount of catalyst with respect to the fibers on which the catalyst is retained. In one or more embodiments, polymer-catalyst assembly 10 includes from 0.5 wt. % to 5 wt. %, in other embodiments, from 0.5 wt. % to 1 wt. %, and in other embodiments, from 0.2 wt. % to 0.25 wt. % of catalyst particles 14. In some embodiments, polymer-catalyst assembly 10 includes 0.2 wt. % or approximate thereto, in other embodiments, 1 wt. % or approximate thereto, and in other embodiments, 5 wt. % or approximate thereto of catalyst particles 14.

Polymer-catalyst assembly 10 may be characterized by the porosity of the assembly or mat. This porosity may be defined as the void spaces between fibers, and may be given as a fraction of the volume of voids over the total volume, between 0 and 1. In one or more embodiments, polymer-catalyst assembly 10 has a mean average porosity of from 0.9 to 0.98, in other embodiments, from 0.9 to 0.92, in other embodiments, from 0.92 to 0.94, and in other embodiments, from 0.95 to 0.98.

In general, higher porosity corresponds to lower pressure drop across polymer-catalyst assembly 10. In one or more embodiments, the pressure drop across the polymer-catalyst assembly 10 with variable upstream flowrate is in the range of from 0.8 kPa to 8.6 kPa, in other embodiments, from 0.8 kPa to 1.1 kPa, in other embodiments, from 1.4 kPa to 4.6 kPa, and in other embodiments, from 7.4 kPa to 8.6 kPa.

In one or more embodiments, polymer-catalyst assembly 10 may be characterized by a basis weight (mass of fibers per area) in the range of from 10 grams per square meter (GSM) to 25 GSM, in other embodiments, from 10 to 15 GSM, in other embodiments, from 15 to 20 GSM, and in other embodiments, from 20 to 25 GSM.

Polymer-catalyst assembly 10 may be characterized by strong attachment of the catalytic particles on the surface of fibers. The strong attachment of the catalytic particles on the surface of fibers may be defined as avoiding leaching of the catalytic particles into the final product. In some embodiments, this may be characterized as the final product not turning black. This avoiding leaching of the catalyst particles in to product is advantageous inasmuch as otherwise leaching of catalyst particles requires an additional separation process.

In one or more embodiments, polymer-catalyst assembly 10 may be used in operation with a reaction fluid. For operation of polymer-catalyst assembly 10 with a reaction fluid, polymer-catalyst assembly 10 may be said to include an inlet in fluid communication with a fluid including a polar reactant. The fluid and polar reactant may be a gas or a liquid. Because catalyst 14 is solid, and therefore available in a different phase than that of reactant and product, catalyst 14 may be characterized as a heterogeneous catalyst.

As mentioned above, based on the polarization of polarized fibers 12, the polar reactant is attracted to polarized fibers 12. Following this attraction, catalyst 14 can thereby function to catalyze a reaction of the polar reactant to a reaction product. The reaction product, which may be nonpolar or less polar than the reactant, is then provided to an outlet of polymer-catalyst assembly 10 where it may be collected as a product. The reactant may be provided continuously and the product may be collected continuously.

In one or more embodiments, polymer-catalyst assembly 10 may be provided within a housing (not shown). Housing may include a planar shaped inlet and a planar shaped outlet parallel, or substantially parallel, with polymer-catalyst assembly 10. Other suitable means for providing polymer-catalyst assembly 10 to a reaction fluid are generally known to those skilled in the art.

A particularly suitable reaction is a hydrogenation conversion, which may be hydrogenation of phenol to cyclohexanone. Hydrogenation is a procedure used to combine a material with hydrogen, particularly to add a hydrogen molecule. Hydrogenation reactions may generally include addition of hydrogen to an unsaturated substance. A suitable reaction method may include providing hydrogen from a hydrogen reservoir for uninterrupted supply during reaction.

Hydrogenation of phenol to cyclohexanone is utilized commercially to produce aliphatic or semi-aromatic polyamides known under the generic designation of nylon. Cyclohexanone is considered as a chief intermediate in the production of superior quality nylon 6 and nylon 66, both generally known to the skilled person. Cyclohexanone may be utilized in the production of adipic acid and ε-caprolactam. Nylon 66 may be produced from adipic acid and Nylon 6 may be produced from ε-caprolactam.

Phenol hydrogenation to produce cyclohexanone is a thermodynamically favored reaction with ΔG=−58.32 KJ/mol. The reaction cannot occur without a catalyst due to the presence of an activation energy barrier.

In the phenol hydrogenation method, it is generally desirable to refrain from producing undesired byproducts such as cyclohexanol. Cyclohexanol may be undesirably produced from the cyclohexanone by the below overall reaction. Where utilized with a phenol hydrogenation reaction, polymer-catalyst assembly 10 preferably has high selectivity of cyclohexanone.

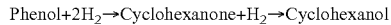

Phenol+2H$_2$→Cyclohexanone+H$_2$→Cyclohexanol

A reaction method including phenol hydrogenation may be characterized by percent conversion of reactants into total products, both desired and undesired. In one or more embodiments, complete or substantially complete conversion of phenol is achieved. In one or more embodiments, complete or substantially complete conversion of phenol is achieved within 9 hours reaction time. In other embodiments, conversion of 74% of phenol is achieved within 9 hours reaction time.

A reaction method including phenol hydrogenation may be characterized by selectivity, which is the percentage of the desired product conversion to the total amount of overall products. In one or more embodiments, complete or substantially complete selectivity of cyclohexanone production compared to cyclohexanol is achieved. In one or more embodiments, complete or substantially complete selectivity of cyclohexanone production compared to cyclohexanol is achieved within 9 hours reaction time. In other embodiments, 78% or approximate thereto selectivity of cyclohexanone production compared to cyclohexanol is achieved within 9 hours reaction time.

In one or more embodiments, polymer-catalyst assembly 10 may be utilized with a reactor having a volume of from 200 mL to 500 mL, in other embodiments, from 200 mL to 300 mL, and in other embodiments, 250 mL or approximate thereto. In one or more embodiments, polymer-catalyst assembly 10 may be utilized with a reactor operated at a temperature of from 70° C. to 100° C., in other embodiments, from 75° C. to 85° C., and in other embodiments, 80° C. or approximate thereto.

In one or more embodiments, polymer-catalyst assembly 10 may be used in operation with a thermal oxidizer. In one or more embodiments, polymer-catalyst assembly 10 may be used in operation with a gas converter.

One or more embodiments of the present invention have industrial applicability as providing a polymer-catalyst assembly having polarized fibers retaining a catalyst, which may be particularly suitable for capturing polar molecules from aqueous based solutions.

In light of the foregoing, it should be appreciated that the present invention advances the art by providing an improved polymer-catalyst assembly and corresponding methods of manufacture and operation. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Example 1

Three different samples were taken in to consideration: a first comparative example composed of as-electrospun PVDF fibers, a second comparative example including electrospun PVDF fibers heated to the Curie temperature (150° C.) but not subjected to polarization, and a representative example including electrospun PVDF fibers that were subjected to polarization (which included heating to the Curie temperature (150° C.)). The comparative examples and the representative example were impregnated with Pd-Black nanoparticles by a wet-impregnation-electrospun (WI-Spun) method to impart the catalytic nanoparticles to the fibers.

The comparative examples and the representative example were then utilized with a phenol hydrogenation reaction. The results showed that the representative example fiber mats increased the catalytic activity and decreased the selectivity by yielding substantial amounts of cyclohexanol alongside with the desired product.

Particularly, the first comparative example of as-electrospun PVDF fibers having Pd-Black nanoparticles as a catalytic support yielded very low catalytic activity of 73±4.76% of overall conversion by the end of 9 hours reaction time. Most of the conversion occurred after the first 6 hours. The as-spun PVDF fibers support recorded 100±0% selectivity. No further activity was observed in prolonged experiments due to leaching of metal catalysts in to the product, due to weak binding interaction between fibers.

The second comparative example of as-electrospun PVDF fibers having Pd-Black nanoparticles as a catalytic support and heated to the Curie temperature (150° C.) reported similar results as as-spun fibers for first 6 hrs. Particularly, the second comparative example had an overall conversion of 32±2.58 and 46±4.16% with 100% selectivity at 3 and 6 hours reaction time, respectively. Using heat-treated fibers yielded high catalytic activity of 100% overall conversion by the end of 9 hours reaction. However, formation of undesired byproducts like cyclohexanol occurred by the end of 9 hours of reaction time. Selectivity of the product was reduced to 78±7.26% due to cyclohexanone formation. Selectivity of cyclohexanone usually decreases with increase in phenol conversion due to the higher concentration of desired product.

For the representative example, the polarized PVDF fibers having Pd-Black nanoparticles as a catalytic support achieved an overall conversion of 73±4.86% in the first 6 hours of the reaction with 100% selectivity. This was almost equal to the conversion rate of the first comparative example at 9 hours. The representative example was the most active material by yielding the highest product conversion. Substantially complete conversion of phenol was achieved within 9 hours reaction time. Moreover, the representative example maintained 100% selectivity toward the desired product at 9 hours reaction time.

Example 2

Figure 5:
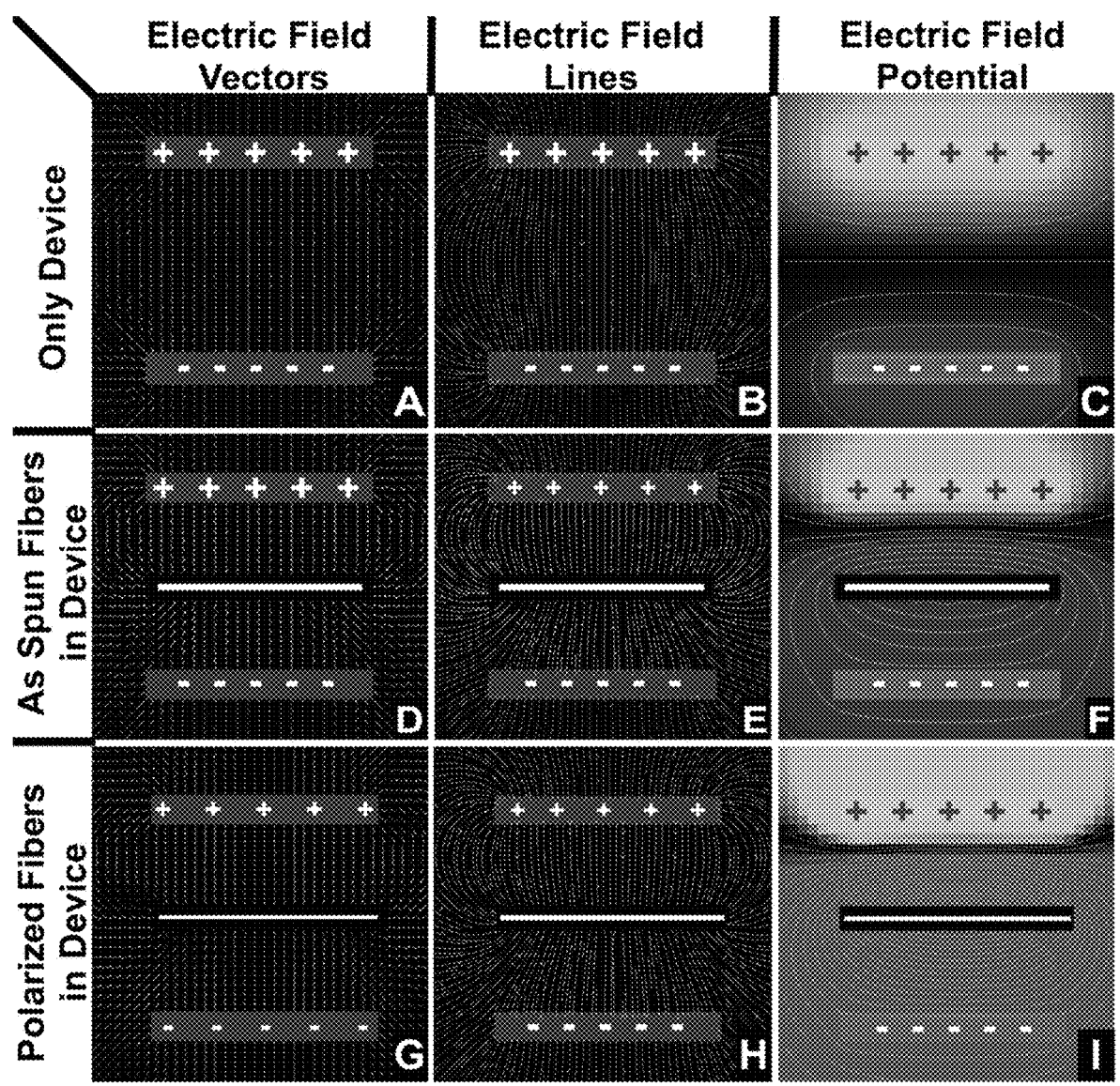
FIG. 5 is a representation of 2D simulations of electric field current density vectors, field lines, and the contour plots of electric potential.

FIG. 5 includes 2D simulations of electric field current density vectors (A, D and G), field lines (B, E and H), and the contour plots of electric potential (C, F and I). The plots in A, B, and C are the simulation results without any fiber mat present. The plots in D, E, and F are simulation results with an as-electrospun un-polarized PVDF fiber mat present. Plots in G, H, and I are results with a polarized PVDF mat present.

The plus and minus symbols indicate aluminum electrodes and the solid white line at the center indicates PVDF fiber mat orientation. In a parallel plate capacitor the electric field of lines travel in the direction from positively charged electrode to the negatively charged electrode as shown in A and B. When a ferro-electric material is placed in between the two electrodes, the dipoles (two equal and opposite charges separated by a small di stance) inside the fibers are aligned in random directions. With the application of strong electric field at elevated temperatures the majority of the dipoles align in a particular direction resulting in net polarization. The surface of the ferroelectric material (the fiber mat) nearest to the positively charged electrode contains the negative charges and vice versa. Hence there is a net change in the electric field lines due to the dipoles in the ferroelectric material as deduced by comparison of B and E. The amount of change in the electric field depends on the strength and concentration of the dipoles in the ferroelectric material. The total current between the electrodes gives a measure of the strength of the polarization of the fiber mats.

Various modifications and alterations that do not depart from the scope and spirit of this invention will become apparent to those skilled in the art. This invention is not to be duly limited to the illustrative embodiments set forth herein.

What is claimed is:

1. A polymer-catalyst assembly comprising polarized polymeric nanofibers retaining a plurality of catalytic metallic nanoparticles, wherein the polarized polymeric nanofibers have an induced dipole moment.

2. The polymer-catalyst assembly of claim 1, wherein the polarized polymeric nanofibers are made of a polymer selected from the group consisting of polyvinylidene fluoride (PVDF), poly(vinylidene fluoride-co-hexafluoropropylene) (PVDF-HFP), polymethyl methacrylate (PMMA), polyvinylchloride (PVC), polytetraflouroethylene (PTFE), polyethylene terephthalate (PET), polystyrene, polyethylene, polypropylene (PP), polycarbonate (PC), polysulfone (PS), and polyamides.

3. The polymer-catalyst assembly of claim 1, wherein the polarized polymeric nanofibers are made of polyvinylidene fluoride.

4. The polymer-catalyst assembly of claim 3, wherein the catalytic metallic nanoparticles are made of Pd.

5. The polymer-catalyst assembly of claim 1, wherein the catalytic metallic nanoparticles are made of a metal selected from the group consisting of Ni, Rh, Ru, Co, Pt, Os, Pd, Au, Pt, Ti, and Ir.

6. The polymer-catalyst assembly of claim 1, wherein the catalytic metallic nanoparticles are made of a metal oxide selected from the group consisting of oxides of Ni, Rh, Ru, Co, Pt, Os, Pd, Au, Pt, Ti, and Ir.

7. The polymer-catalyst assembly of claim 1, wherein the catalytic metallic nanoparticles are made of Pd.

8. The polymer-catalyst assembly of claim 1, wherein the induced dipole moment within the polarized polymeric nanofibers is from $4.63 \times 10^{-12}$ coulomb-meter (C·m) to $7.35 \times 10^{-12}$ C·m.

9. The polymer-catalyst assembly of claim 1, wherein the polarized polymeric nanofibers have a mean average cross-sectional diameter of from 50 nm to 300 nm.

10. A method of making the polymer-catalyst assembly of claim 1 comprising
providing a fiber mat having polymeric nanofibers retaining a plurality of catalytic metallic nanoparticles,
stretching the fiber mat in a uniaxial direction,
simultaneous with the step of stretching, thermally heating the fiber mat,
simultaneous with the steps of stretching and thermally heating, subjecting the fiber mat to an electric field,
whereby the simultaneous steps of stretching, thermally heating, and subjecting thereby form a polarized fiber mat.

11. The method of claim 10, wherein the step of providing the fiber mat includes electrospinning a spinnable solution to form an electrospun fiber mat.

12. The method of claim 11, wherein the step of providing the fiber mat includes soaking the electrospun fiber mat in a solution containing a precursor of the catalytic metallic nanoparticles, the method further comprising a step of reducing the precursor to form the catalytic metallic nanoparticles.

13. The method of claim 10, the fiber mat having an un-stretched length, wherein the step of stretching the fiber mat includes stretching the fiber mat from 1.1 to 1.15 times the un-stretched length.

14. The method of claim 10, wherein the step of thermally heating the fiber mat includes subjecting the fiber mat to a constant temperature ramp rate of from 15° C./min to 25° C./min.

15. The method of claim 10, wherein the electric field is in a range of from 2 kV/cm to 3 kV/cm.

16. The method of claim 10, further comprising a step of cooling the polarized fiber mat.

17. The method of claim 10, further comprising a step of providing a reaction fluid containing phenol to the polarized fiber mat.

18. The method of claim 17, wherein the step of providing a reaction fluid containing phenol to the polarized fiber mat achieves substantially complete conversion of phenol.

19. The method of claim 17, wherein the step of providing a reaction fluid containing phenol to the polarized fiber mat achieves substantially complete conversion of phenol to cyclohexanone within 9 hours reaction time.

20. The method of claim 17, wherein the step of providing a reaction fluid containing phenol to the polarized fiber mat achieves substantially complete selectivity of cyclohexanone.

* * * * *